(12) United States Patent
Hor et al.

(10) Patent No.: US 9,030,286 B2
(45) Date of Patent: May 12, 2015

(54) METAMATERIALS WITH TERAHERTZ RESPONSE AND METHODS OF MAKING SAME

(75) Inventors: Yew Li Hor, Singapore (SG); Hee Chuan Lim, Houston, TX (US); Yew Fong Hor, Houston, TX (US); John Francis Federici, Westfield, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 194 days.

(21) Appl. No.: 12/755,785

(22) Filed: Apr. 7, 2010

(65) Prior Publication Data

US 2010/0271692 A1    Oct. 28, 2010

Related U.S. Application Data

(60) Provisional application No. 61/167,745, filed on Apr. 8, 2009.

(51) Int. Cl.
| | |
|---|---|
| *H01F 27/30* | (2006.01) |
| *G02B 1/00* | (2006.01) |
| *H01P 1/203* | (2006.01) |
| *H01P 7/08* | (2006.01) |
| *H01Q 15/00* | (2006.01) |
| *G01N 21/3581* | (2014.01) |

(52) U.S. Cl.
CPC ............ *G02B 1/007* (2013.01); *G01N 21/3581* (2013.01); *H01P 1/20381* (2013.01); *H01P 7/082* (2013.01); *H01Q 15/0026* (2013.01); *H01Q 15/0086* (2013.01)

(58) Field of Classification Search
CPC ............. A01B 12/006; H01Q 15/0026; H01Q 15/0086; G01N 21/3581
USPC ........ 428/209; 361/760; 340/572.7; 336/200, 336/205, 206, 208

See application file for complete search history.

(56) References Cited

U.S. PATENT DOCUMENTS

| | | | | |
|---|---|---|---|---|
| 6,107,920 A | * | 8/2000 | Eberhardt et al. | 340/572.7 |
| 6,164,551 A | * | 12/2000 | Altwasser | 235/492 |
| 6,445,271 B1 | * | 9/2002 | Johnson | 336/200 |
| 6,595,426 B1 | * | 7/2003 | Brunet et al. | 235/487 |
| 6,665,193 B1 | * | 12/2003 | Chung et al. | 361/760 |
| 7,082,834 B2 | * | 8/2006 | Petrova et al. | 73/708 |

* cited by examiner

*Primary Examiner* — Cathy Lam
(74) *Attorney, Agent, or Firm* — Timothy X. Gibson, Esq.; Gibson & Dernier LLP (57) ABSTRACT

Flexible metamaterials and three-dimensional metamaterials operable in the terahertz range are disclosed. Methods are disclosed for fabricating terahertz response metamaterials using microfluidic-jetted techniques. Layers of material including substrate and deposited material are stacked to form three dimensional bulk metamaterials. The fabricated metamaterials act as left-handed metamaterials in the range 0.1 to 3.0 THz.

16 Claims, 13 Drawing Sheets

METAMATERIALS WITH TERAHERTZ RESPONSE AND METHODS OF MAKING SAME

CROSS-REFERENCE TO RELATED APPLICATIONS

This application claims the benefit of U.S. Provisional Patent Application No. 61/167,745 filed Apr. 8, 2009, the entirety of which is incorporated herein by reference.

FIELD OF THE INVENTION

This invention relates to metamaterials and in particular, to metamaterials having a terahertz response and methods of making same.

BACKGROUND OF THE INVENTION

Natural materials have some restrictions on their electromagnetic properties. It is difficult to find a natural material which has the necessary properties or material parameters required for certain applications. This problem usually can be solved by using metamaterials.

Metamaterials (hereinafter referred to as MTMs) are defined as artificial materials which achieve extraordinary electromagnetic properties that are not possible in natural material. Although composite materials have been investigated for many years, MTMs really form a new field of science and engineering. If one considers the first demonstration to be from 2000-2001 by Pendry et. al. as the commencement of MTMs, this field is less then 10 years in 2008. See, Composite Medium with Simultaneously Negative Permeability and Permittivity; Smith, D. R., Padilla, W. J., Vier, D. C., Nemat-Nasser, S. C., Schultz, S.; 2000, *Physical Review Letters* 84 (18), pp. 4184-418.

The index of refraction of MTMs is considered to be negative when the effective permittivity and permeability are simultaneously negative. As a consequence of their double negative parameters, plane waves propagating in such metamaterials are characterized by antiparallel phase and group velocities and reversal of wave vector that follow a left-hand rule, thus giving rise to the name left-handed (meta) materials (LHM). This type of material has been named by Veselago as left-handed material (LHM) V. G. Veselago, The electrodynamics of substances with simultaneously negative values of $\epsilon$ and $\mu$, *Sov. Phys. Usp.*, 10, pp. 509-514, (1968).

Experiment and simulation have confirmed that the LHMs do indeed exhibit negative refraction. R. A. Shelby, D. R. Smith, S. Schultz, Experimental verification of a negative index of refraction, *Science*, 292 (5514), pp. 77-79, (2001). However, the experiment by Shelby was conducted in the microwave region and the sample investigated was a bulk three-dimensional prism slab.

Although THz-TDS has been proposed as a technique for measuring the index of refraction of MTMs, see, J. Han, Probing negative refractive index of metamaterials by terahertz time domain spectroscopy, *Opt. Exp.*, 16 (2), pp. 1356, (2008), a negative index of refraction in the terahertz region has not yet been observed. Materials exhibiting a magnetic response are extremely rare in THz and optical frequencies because magnetic phenomena tend to occur at far lower frequencies. Certain ferromagnetic and antiferromagnetic materials such as InGaMnAs/InP and GdMnO3 exhibit a very weak magnetic response over a frequency range of several hundred gigahertz which limit the scope of possible THz devices. Nearly all of the MTMs that exist in the terahertz region are single, two-dimensional layers fabricated on a rigid substrate due to the limitation of the conventional MEMs technique. This is mainly due to the inability in fabricating the MTMs into a bulk three-dimensional slab. Thus there is a need for alternative, advanced and simplified MTMs that can be easily fabricated and characterized, and methods for making such MTMs.

SUMMARY OF THE INVENTION

Embodiments of the present disclosure provide metamaterial (MTM) structures in the THz range. MTMs in accordance with the present disclosure enable an artificial magnetic component for the implementation of devices at THz frequencies such as THz sources, harmonics generators, photo mixers and the like. Metamaterials made in accordance with the present disclosure also make possible the development of novel devices for biological and security sensing and are used as antenna radomes or as a frequency selective surface to control the direct emission of radiation sources.

In accordance with one embodiment flexible two-dimensional metamaterials are provided. A flexible substrate includes a suitable material patterned thereon operable to act as a flexible metamaterial operable in the THz range.

In accordance with another embodiment three-dimensional metamaterials are provided essentially comprising multiple layers of substrate, each substrate having a suitable material deposited thereon in a pattern operable to permit the layered structure to act as a metamaterial operable in the THz range. The substrate may be flexible material as described herein.

In accordance with another embodiment, a novel method of fabrication of MTMs is disclosed employing a microfluidic-jetted technique for making two- and three-dimensional conventional MTMs in the terahertz region. Using this novel method, for the first time MTMs can be fabricated on a flexible substrate, thus adding the potential for future market applications. In addition, using the microfluidic-jetted technique, miniature three-dimensional THz MTMs can be achieved by stacking the two-dimensional structures in layers. Microfluidic-jetting is a variation of ink-jet printing techniques and is currently being evaluated as a precision deposition tool in a variety of manufacturing processes such as Liquid Crystal Display (LCD) and Organic Light Emitter Diode (OLED). See, W. Wong, Inkjet printer draws the line in manufacturing technology, *Electronic Design*, 53 (25), 25, (2005); J. C. Sturm, et al., Printing approaches for large-area color organic LED displays, *Proc. of SPIE—The International Society for Optical Engineering*, 3797, 266-274, (1999); S. C. Chang, et al., "Multicolor organic light-emitting diodes processed by hybrid inkjet printing," *Adv. Materials*, 11 (9), 734-737, (1999). The methods disclosed herein provide economic advantages in cases in which the deposited material is expensive. By eliminating the use of die or photomask the presently disclosed methods reduce fabrication cost and minimize fabrication time, resulting in the ability to prototype rapidly. In addition, the microfludic-jetted technique offers the advantage of non-contact, thus minimizing risk of contamination. The methods can be used in conjunction with any suitable substrate and can be used to deposit a wide variety of material, thereby providing great design flexibility. The nozzle sizes of the microfluidic jet can be varied depending on the application and the desired design.

Given above is a simplified summary of the disclosure in order to provide a basic understanding of some aspects described herein. The advantages described herein and others will be apparent to those having skill in the art.

BRIEF DESCRIPTION OF THE DRAWINGS

To assist those of ordinary skill in the relevant art in making and using the subject matter hereof, reference is made to the appended drawings, wherein.

It should be noted that the appended drawings illustrate only typical embodiments of this invention and are therefore not to be construed as limiting of its scope, for the invention may admit to other equally effective embodiments.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

As described in further detail hereinbelow, flexible terahertz region metamaterials are constructed using microfluidic-jetted methods. Fabrication of the metamaterials essentially comprises providing a substrate and depositing suitable material in a desired pattern on the substrate using microfluidic-jetted deposition techniques. Three-dimensional metamaterial structures in the THz range may be produced by stacking layers of substrates produced using the described deposition techniques.

It will be apparent to the skilled artisan that the substrate should be chosen for properties that are consistent with use in a metamaterial structure. It is desirable for the substrate material to meet the following criteria: minimal lateral cross sectional expansion due to the surrounding thermal fluctuation, flexible, ductile, robust, shock resistant, and transparent to THz electromagnetic waves. Examples of suitable substrates include polyimide such as Kapton® polyimide film available from DuPont, Pyralux® copper cladded polyimide film, Mylar® polyester film, and the like. The substrate should be flexible.

It will be apparent to the skilled artisan that the deposited material should be chosen for properties suitable for use in a metamaterial structure. It is desirable for a deposited material to meet the following criteria: highly electrically conductive, low thermal expansion, low brittleness, low fragility, low vaporization and optimum viscosity of about 10 cps for inkjet printing Examples of suitable deposited material include metals such as gold; copper; silver; group III-V compound semiconductors such as donor atoms like selenium, tellurium, germanium, silicon, etc. and acceptor atoms like beryllium, cadmium, zinc, etc.; group IV semiconductors such as donor atoms like arsenic, phosphorus, etc. and acceptor atoms like boron, aluminium, etc.; highly electrical conductive polymers such as poly(3,4-ethylenedioxythiophene)poly(styrenesulfonate)(PEDOT:PSS), (3,4-ethylenedioxythiophene)-block-poly(ethylene glycol), etc.; highly electrically conductive liquid metal such as indium tin oxide, gallium; nano metallic particles such as nano silver and nano gold; both metallic and semiconductor single walled carbon nano tubes; both metallic and semiconductor multi walled carbon nano tubes; colloidal graphite; colloidal silver liquid; and the like. The deposited material may be a functionalized nanoparticle such as but not limited to dodecanethiol functionalized nano-gold, semiconductor and metallic carbon nano tubes in aqueous suspension, liquid indium tin oxide, liquid gallium, colloidal graphite, colloidal silver liquid, or the like in a carrier fluid suitable for use in a microfluidic cartridge.

The pattern of the deposited material is designed to act as a metamaterial. Suitable patterns for a two-dimensional metamaterial include a periodic Slot Ring Resonator (SRR), periodic microstrip, periodic monolithic rod, periodic horseshoe, periodic polygonal, periodic windmill, periodic swastika, periodic circular, periodic oval, periodic square grids, and the like in large scale 2D matrix layout. Suitable patterns for a three-dimensional metamaterial include a periodic SRR, microstrip, periodic monolithic rod, periodic horseshoe, periodic polygonal, periodic windmill, periodic swastika, periodic circular, periodic oval, periodic cubical grids, and the like in large scale 3D matrix layout, wherein the patterns are layered in the following possible configurations: periodic alternating SRR/microstrip layers, alternating monolithic rod/microstrip layers, alternating horseshoe/microstrip layers, and the like in large scale matrix layout in large scale 3D matrix layout.

Examples of suitable carrier fluid formulations include xylene, 4-methylpentan-2-one, 3% ethanol, toluene pure grade, hexane pure grade, butyl acetate, acetone, hexone, 2-Propanol, deionized water, 4-methyl-2-pentanone, isobutyl methyl ketone, propylene glycol, monoethyl ether, ethyl acetate, propylene carbonate, nitromethane, and the like. It is desirable for carrier fluid formulations to meet the following criteria: have a viscosity of about 10-15 cps, surface tension of about 28-33 dynes, a stability wherein the boiling point is greater than about 100° C., and a minimum amount of dissolved gas. Since such gas could inhibit jetting, it should be removed by filtration.

The substrate should be cleaned, such as with a cleaning agent and/or ultrasonic treatment to remove unwanted particles or impurities. The materials to be deposited are loaded in a microjet cartridge. The desired pattern layout is designed, such as by using a pattern editor that allows a user to design and select proper drop spacing (preferably with a minimum of about 5 micrometers) for the pattern layout. Suitable commercially available pattern editors include Adobe Postscript Writer, Dimatix Built-in Pattern Editor/Designer, etc.

The cartridge mounting angle is adjusted to the appropriate angle. The proper cartridge mounting angle will depend on the drop spacing that is selected and the nozzle size of the microjet. The waveform setting should be adjusted to control the jetting performance by controlling the percent of amplitude, slew rate and jetting duration of the silicon piezo diaphragm at the nozzle. The cartridge setting should be adjusted to control the drop quality and volume, by adjusting the voltage, temperature, drop meniscus, print height and cleaning process cycle.

Drop sizes are dependent on the application, including the dimensions of the patterned material as deposited on the substrate, the composition of the deposited material and the substrate. Exemplary suitable drop sizes range from about ±1 µm to about ±5 µm.

Commercially available cartridges that are suitable for the presently disclosed methods include SX3 Printhead, SE3 Printhead, and 1 and 10 picoliter DMP cartridge printheads by Dimatix by Fujifilm Inc., XY Materials Deposition System (XYMDS) from iTi Corporation, MSV 2500i Ink Jet material deposition tool by M-SOLV Limited, Seiko Epson Micro Piezo inkjet printheads and the like. These cartridges may be used in printers commercially available from imaging Technology international Corporation (iTi), OptoSigma Corporation, FujiFilm Inc, Seiko Epson Corporation, M-SOLV Limited, and to carry out the deposition step.

Nozzle size of the microfluidic jet can be varied, depending on the application and the desired design. Suitable nozzle sizes may vary for example from 9 to 2.15 micrometers.

The following examples are illustrative.

Example 1

Figure 1:
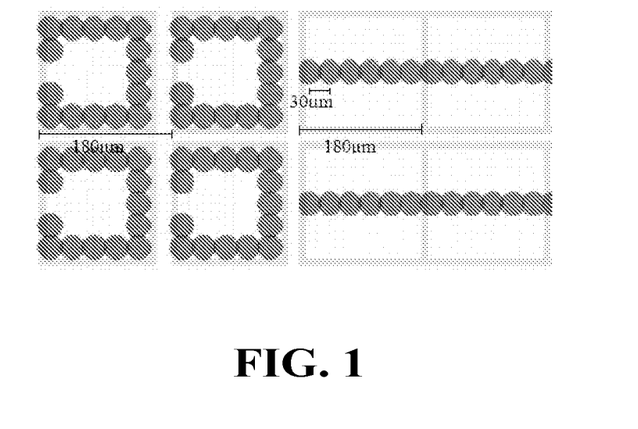
FIG. 1 depicts an image of a bitmap layout of a conventional split-ring resonator (left) and microstrips (right) pattern in accordance with an aspect of the present disclosure.

Now referring to FIG. 1, patterns of split ring resonator (SRR) and microstrips structures were deposited on top of a copper-clad Kapton® polyimide sheet with liquid polyimide using a microfluidic-jetted technique by microdroplet generation of approximately 1 pL. The liquid polyimide was purchased from HD MicroSystem® and mixed with a solvent, Pyralin thinner, in a ratio of 1:8 parts. This fluid is supplied as a solution suitable for the coating application. It can be coated onto a variety of metals and is inert with respect to the etchant, thus it is suitable to use as masking material for fabrication of copper samples. The microdroplets were placed drop by drop on the substrate to form the final desired pattern. The patterned copper clad Kapton sheet was then subjected to an etching process before it was annealed at 160° C. for 30 minutes. The deposited polyimide patterns act as a mask to prevent the copper under the pattern from being etched away by the etchant.

Figure 2:
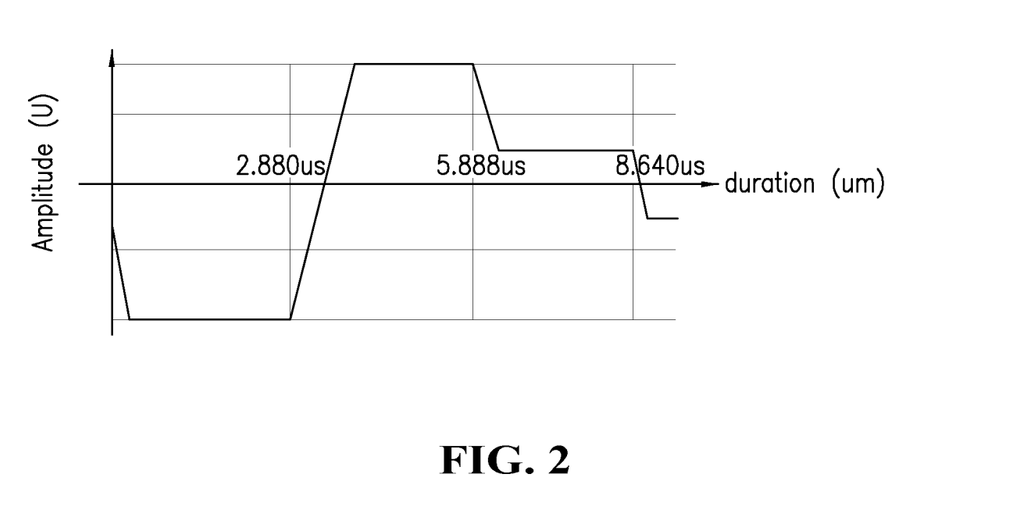
FIG. 2 is a graphical depiction of a waveform setting of liquid polyimide in accordance with an aspect of the present disclosure.
Figure 3:
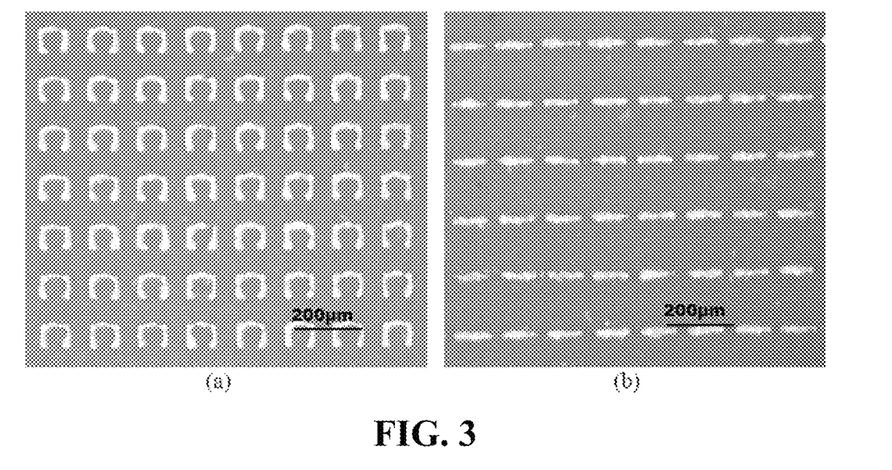
FIG. 3(a) is a bright field microscope image of a copper SRR having a lattice size of 180 µm in accordance with an aspect of the present disclosure.
FIG. 3(b) is a bright field microscope image of microstrips having a lattice size of 180 µm in accordance with an aspect of the present disclosure.
Figure 5:
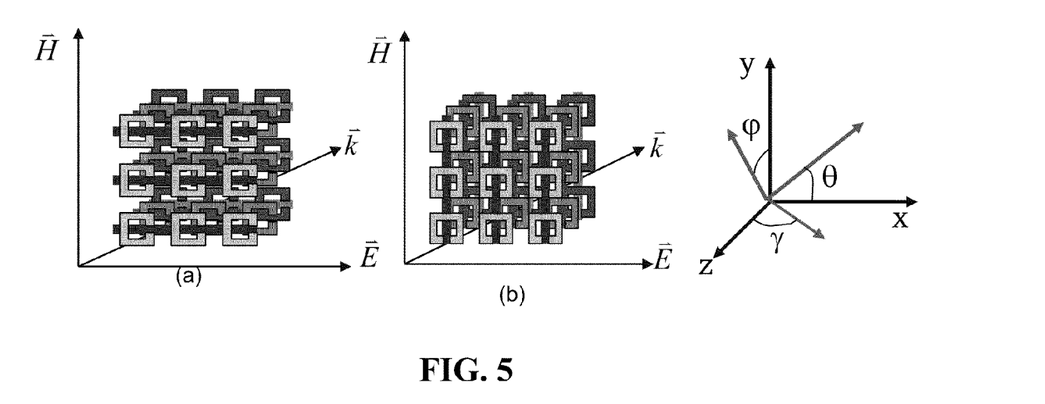
FIG. 5(a) is a graphical depiction of a case 1 orientation of a sample relative to the incident wave propagation wherein the E-field is perpendicular to the open gap of a SRR in accordance with an aspect of the present disclosure.
FIG. 5(b) is a graphical depiction of a case 2 orientation of a sample relative to the incident wave propagation wherein the E-field is parallel to the open gap of a SRR in accordance with an aspect of the present disclosure. A key is included in FIG. 5(b) indicating axis labels.

Table 1 and FIG. 2 show the cartridge and waveform setting for optimum liquid polyimide jetting, respectively. FIGS. 3(a) and (b) show the final product of the samples. These SRR and microstrip samples were then stacked in layers (as can be seen in FIGS. 5(a) and (b)) to form a three-dimensional left-handed metamaterial which simultaneously possesses a negative index of refraction, negative permittivity and negative permeability.

TABLE 1

List of cartridge setting of liquid polyimide

| Fluidic | Liquid polyimide |
|---|---|
| Jetting voltage (V) | 19-21 |
| Meniscus pressure (inches H$_2$O) | 3 |
| Print height (mm) | 0.6 |
| Print height (mm) | 0.6 |
| Nozzle temperature (° C.) | 28 |

Figure 4:
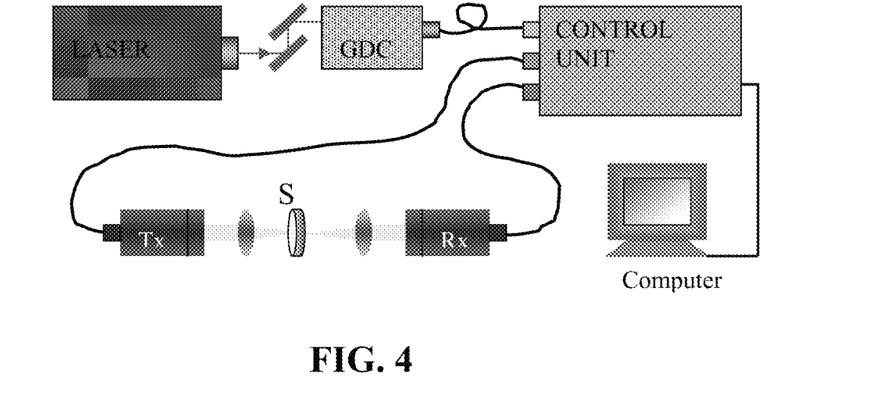
FIG. 4 depicts a layout of a spectroscopy system employed to measure the THz time-domain waveform of a sample in accordance with an aspect of the present disclosure.

Now referring to FIG. 4, a T-ray 2000 Spectroscopy system (Picometrix, Inc.) was used in the transmission mode to measure the THz time-domain waveform of the sample. The sample S was placed in between the terahertz transmitter Tx and detector Rx in two orientations as shown in FIGS. 5(a) and (b): in case 1 (FIG. 5(a)), the SRR gap is parallel to the E-field and in case 2 (FIG. 5(b)), the SRR gap is perpendicular to the E-field. The THz time domain waveforms were acquired by recording the THz transmitted pulse at each sample orientation. Spectral information as a function of frequency, phase and amplitude was acquired through a Fourier transform of the time-domain data.

Figure 6A:
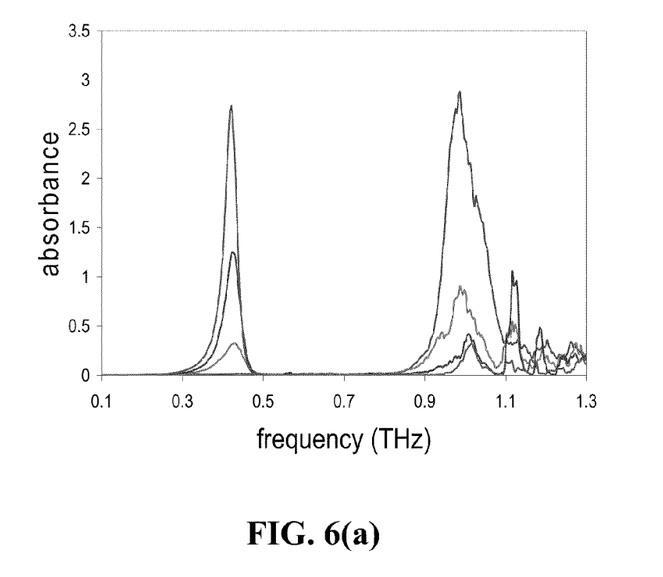
FIG. 6(a) is a graphical depiction of measured data with THz signal propagated into the plane of a SRR sample in accordance with an aspect of the present disclosure; the sample is rotated in xy-plane (sample plane) from 0° (blue), 30° (orange), 60° (purple) and 90° (green)

Now referring to FIGS. 6(a)-6(d), the data obtained from the copper sample for both SRR and break-microstrips when the incident wave is perpendicular to the sample plane is shown. The data was measured with the sample oriented from θ=0° (case 1) to 90° (case 2) in the x- and y-plane. FIG. 6(a) shows the absorbance spectra of SRR. There are two absorbance maxima in the spectra, one located at 0.42 THz and the other located at 0.98 THz. For case 1, the absorbance maximum is observed at 0.98 THz only. For case 2, a major peak is observed at 0.43 THz and a secondary minor peak is at 0.98 THz. The different angular dependences of the two absorbance peak suggested that the SRR should act not only as a magnetic dipole, but also as an electric dipole as discussed in detail by Marqués et al., Ab initio analysis of frequency selective surfaces based on conventional and complementary split ring resonators, *J. Opt. A,* 7 (2), 38-43, (2005) and Chen et al., Experimental verification of standing-wave plasmonic resonances in split-ring resonators, *Appl. Phys. Lett.,* 93 (3), 034110, (2008). It will be noted the first resonance comes from the magnetic response, and the second resonance comes from electric response which is known as a plasmonic resonance.

Figure 6B:
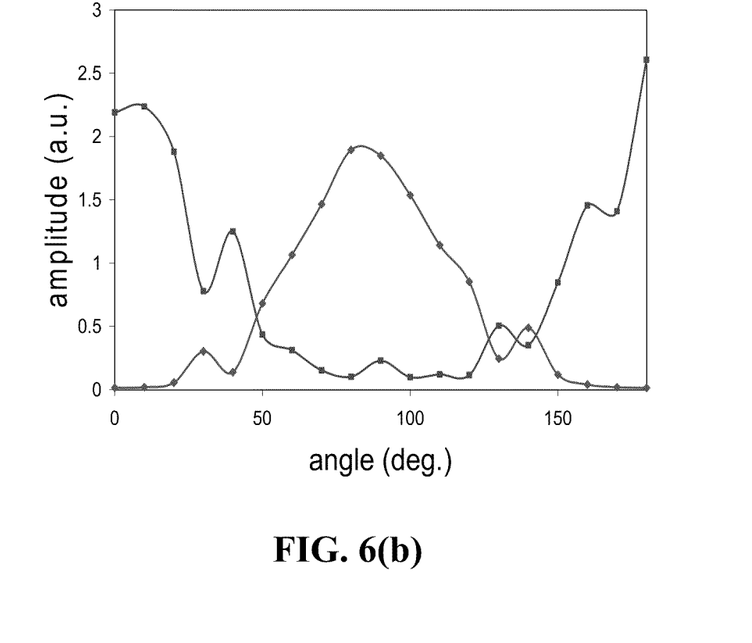
FIG. 6(b) is a graphical depiction of the amplitude of the peak due to its rotation angle for the SRR sample at peak 0.43 THz (green) and 0.95 THz (blue) in accordance with an aspect of the present disclosure.

FIG. 6(b) shows the angular dependence of SRR of the sample. The blue and green curves indicate the amplitude of the absorbance at 0.43 THz and 0.98 THz, respectively. These responses are expected to form sine or cosine function as the angles rotate in cycle. But the experiment result exhibited deviation from simple sine/cosine function. This is explained by imperfections in the fabricated sample. The changes of the absorbance amplitude relative to the rotated angle in the sample plane are due to the fact that E-vector and the SRR gap were changed from parallel to perpendicular.

Figure 6C:
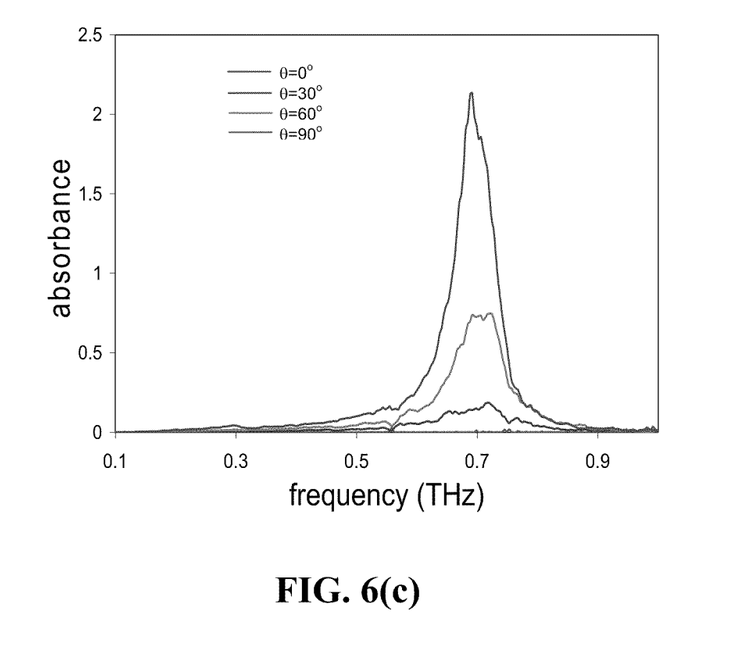
FIG. 6(c) is a graphical depiction of measured data with THz signal propagated into the plane of a microstrips sample in accordance with an aspect of the present disclosure; the sample is rotated in xy-plane (sample plane) from 0° (blue), 30° (orange), 60° (purple) and 90° (green)
Figure 6D:
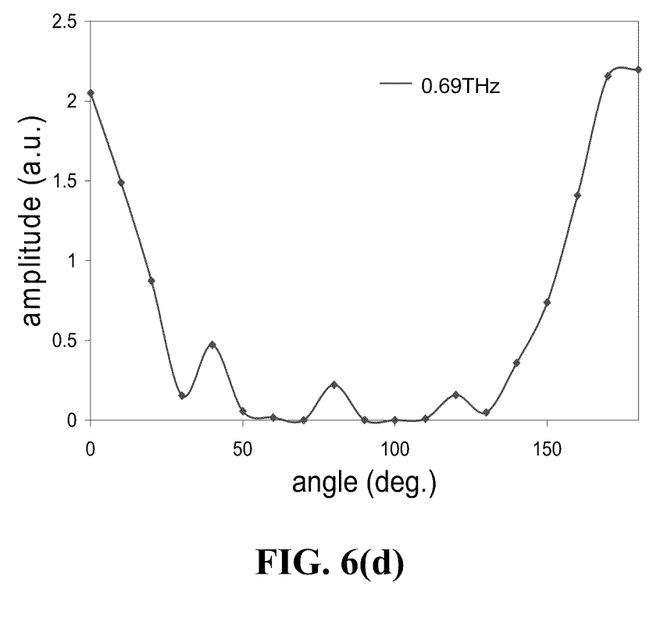
FIG. 6(d) is a graphical depiction of the amplitude of the peak due to its rotation angle for the microstrips sample at peak 0.69 THz in accordance with an aspect of the present disclosure.

FIGS. 6(c) and (d) shows the absorbance spectra and angular dependence of the microstrips which indicates a significant absorbance peak at 0.69 THz for 0° where the strips are parallel to the E-field. The microstrips have only an electric response due to its symmetric nature.

Figure 7:
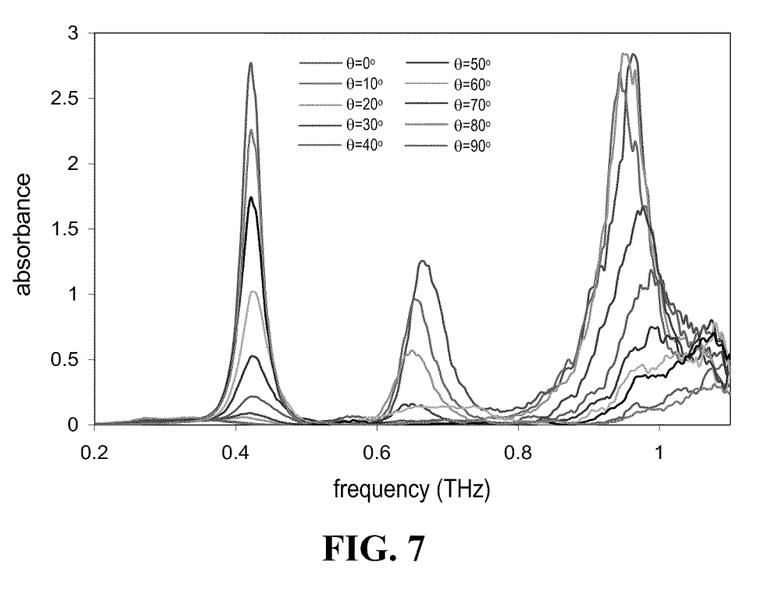
FIG. 7 is a graphical depiction of an experimental result of a copper sample in accordance with an aspect of the present disclosure. The sample was measured in THz wave incident to the sample plane and the sample was rotated from θ=0° to 90° in xy-plane.
Figure 8:
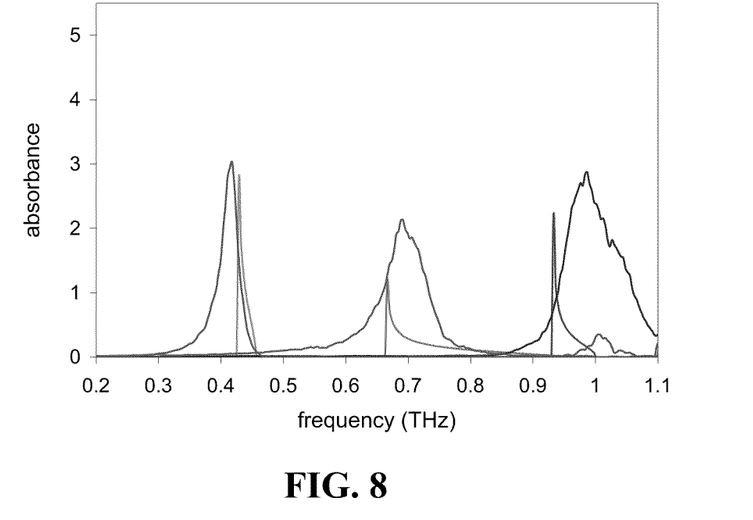
FIG. 8: is a graphical depiction of a comparison of simulation and experimental absorbance of copper SRR and break-microstrips in accordance with an aspect of the present disclosure.
Figure 9A:
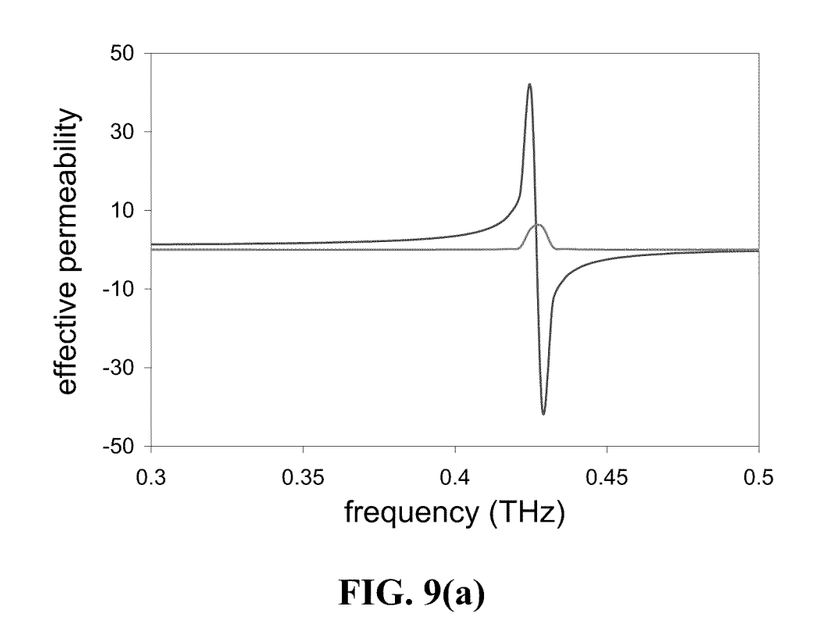
FIGS. 9(a)-9(d) are graphical depictions of a simulation result of effective permeability (FIG. 9(a)), effective permittivity of SRR (FIG. 9(b)), effective permittivity of break microstrips (FIG. 9(c)), and refractive index of 3D copper LHM (FIG. 9(d)) in accordance with an aspect of the present disclosure.
Figure 9B:
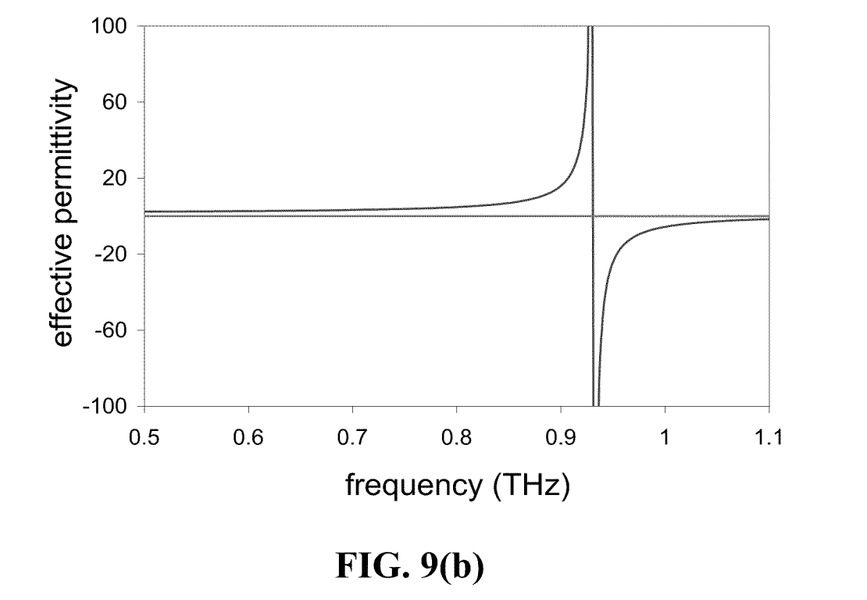
Figure 9C:
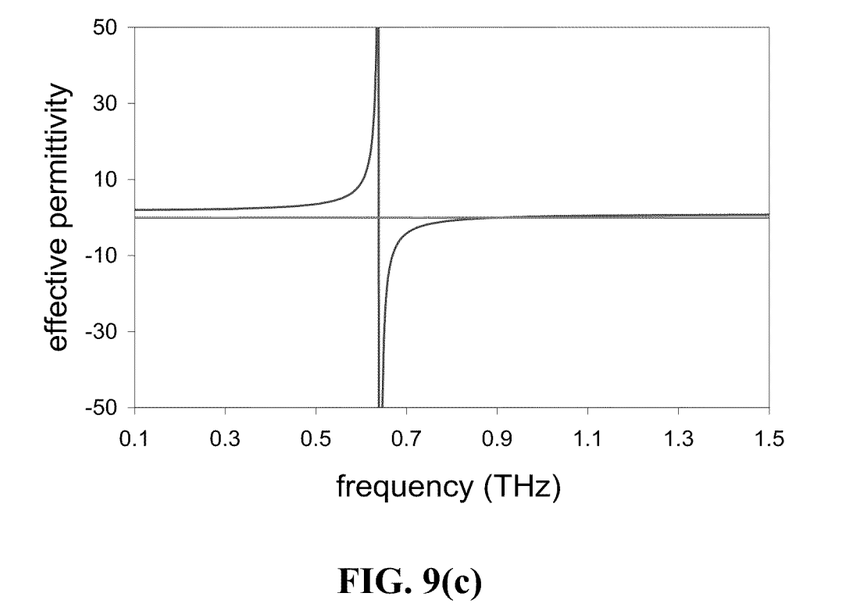
Figure 9D:
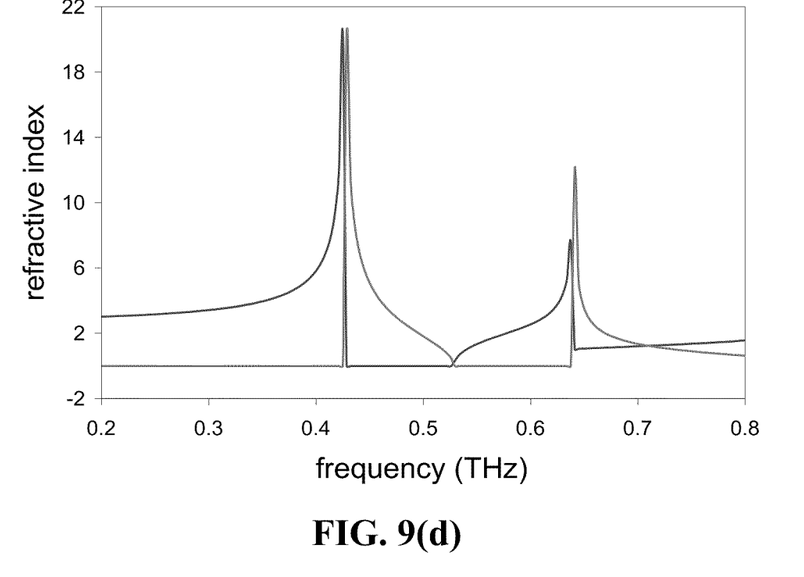

FIG. 7 shows the absorbance peak of the copper LHM. FIG. 7 indicates the LHM exhibits the combination of results for the individual copper SRR and microstrips (see FIGS. 6(a)-(d)). The first and third absorbance peak located at 0.43 THz and around 0.98 THz, respectively, are a consequence of an electric coupling magnetic response of the SRR structure. The second absorbance peak located at 0.69 THz is the result from electrical response of the microstrips. The major distinguishable phenomenon from the results of the LHM and individual SRR/microstrips is the shifting of the second and the third absorbance peak. The third absorbance peak shifts to higher frequency for larger θ. It is believed this phenomenon is due to the human error in alignment of the sample to the incident k-vector. The sample may have a small angle tilted from xy-plane that caused this shifting of peaks.

It is known from fundamental electromagnetism theory that a magnetic dipole can be realized by the circulating current of a closed metallic loop which leads to a magnetic moment. The magnitude of the magnetic moment is given by the product of the current and the area of the loop and its direction is perpendicular to the plane of the loop contributed to stored magnetic energy which relates to the self-inductance, L, of the loop. If a cut is made in the loop, then its acts like a capacitor, with capacitance C. One obtains an LC circuit, with a resonance frequency $$\omega_{LC} = \frac{1}{2\pi\sqrt{LC}} \quad (1)$$

Thus, a SRR acts like an electromagnetic resonator producing $\omega_{LC}$ resonant circular currents and a resonant magnetization, i.e., resonant effective permeability.

The order of magnitude of the resonance frequency for such an SRR can be estimated by considering the SRR capacitance in the area of its gap, treating the gap as a parallel plate capacitor with $$C_{SRR} = \varepsilon_0 \varepsilon_c \frac{wt}{d_{gap}} \quad (2)$$

where w is width of the SRR side, $d_{gap}$ is the width of the gap, t is the thickness of the structure, and $\epsilon_c$ is the relative permittivity of the material in the gap of the capacitor. The inductance formula of the SRR is $$L_{SRR} = \mu_o \frac{a_x a_y}{t} \quad (2)$$

where $a_x$ and $a_y$ are the length of the SRR in x and y, respectively. By Applying Drude theory and Kirchoff rule in effective permittivity and permeability, the generic frequency of the effective permeability is obtained (see Soukoulis et al., Negative index materials: New frontiers in optics, *Adv. Materials,* 18 (15), 1941-1952, (2006)) as $$\mu_{eff}(\omega) = 1 + \frac{F\omega^2}{\omega_{LC}^2 - \omega^2 + i\zeta\omega} \quad (3)$$

By comparing these equations, one can conclude $\omega_{LC}$ is analogous to $\omega_{om}$ in Equation 5. The filling factor, F, and damping constant, ζ, are constants relating to the geometry and materials composing the artificial medium. In an SRR, the filling factor is simply equal to $$F = \frac{a_x a_y}{p^2} \tag{4}$$

and the damping constant of SRR is defined in Equation 7.

The infinite microstrips medium alone can be characterized by an effective permittivity having the same form as a dilute, collisionless plasma, which is define in Equation 2. Inductance and capacitance for infinite microstrips are $$L_{infMS} = \frac{\mu_o l}{2\pi} \ln\left(\frac{2l}{w}\right) \tag{5}$$

$$C_{infMS} = \varepsilon_o \varepsilon_r l \tag{6}$$

in which l is the length of the microstrips. In this case, l is equal to lattice length, p. Thus, by applying Equation 1, the plasma resonance of infinite microstrips is $$\omega_{pe} = \frac{2\pi \cdot c}{p} \sqrt{\frac{1}{\ln\left(\frac{p}{w}\right)}} \tag{7}$$

Typically, in the quasi-static regime, the effective permittivity of infinite lattices of unloaded wires is described using the Drude model. However, for a semi-finite microstrips medium, effective permittivity is deduced (see, Ikonen et al., Mesoscopic effective material parameters for thin layers modeled as single and double grids of interacting loaded wires, *Metamaterials*, 1 (2), 89-105, (2007)) to $$\varepsilon_{eff}(\omega) = 1 - \frac{\omega_{LC}^2}{\omega^2 - \omega_{LC}^2 + i\omega\zeta} \tag{8}$$

Figure 10:
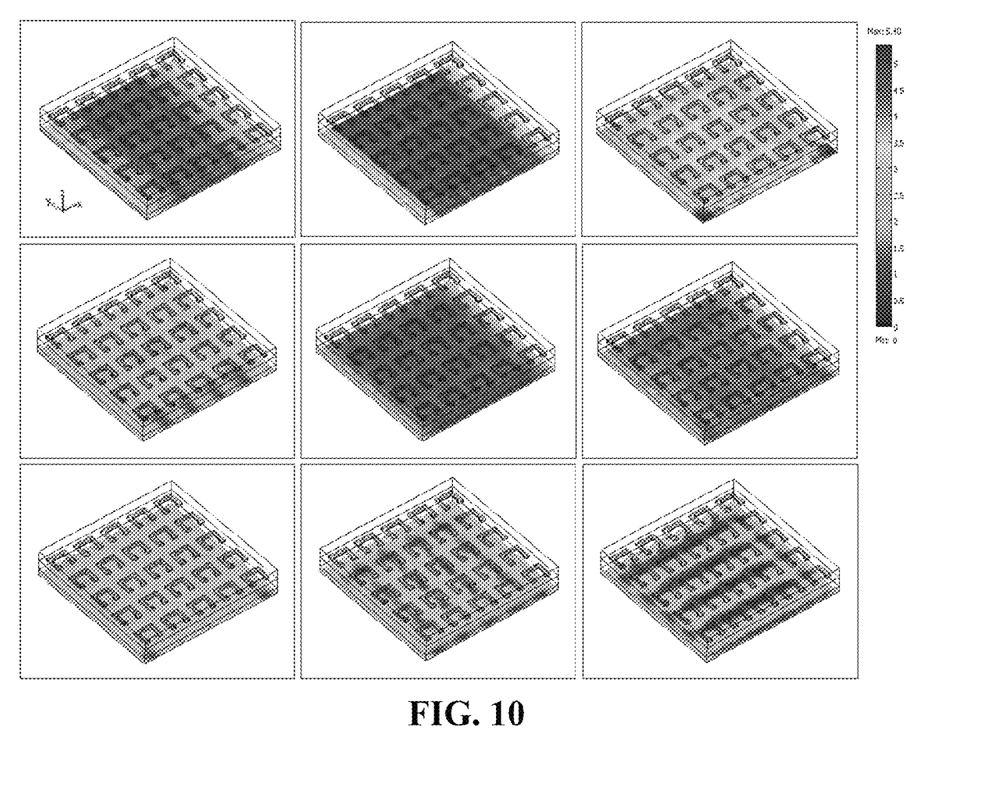
FIG. 10 depicts multiple views of a three-dimensional model of 10×10 copper SRR: a surface plot of a normalized electric field from frequencies 0.2 to 1 THz in accordance with an aspect of the present disclosure. The resonance frequencies are shown at 0.4 and 0.8 THz. The color bar indicates the scale in V/m.

By applying Equations 1 to 8, the effective ε and μ parameters are retrieved and FIGS. 9 and 10 show both the simulation and experimental results for copper SRR and break-microstrips.

FIG. 10 shows the simulation of the copper SRR in a three-dimensional approach using a FEMLAB RF module. The result shows that there is a major resonance peak falling at 0.4 THz and a small resonance peak 0.8 THz. The simulation result in this model has proven to match with the experimental and previous calculation using Excel add-in. However, since the run time in this simulation is very large and also consumes large RAM and cache memory, simulation in fine step size of frequencies and fine mesh sizes could not be performed. A better machine is needed for a more accurate simulation.

The samples in this example were fabricated by a combination of a microfluidic-jetted technique and a typical PCB etching technique. MTMs fabricated using this combination technique was first discovered and realized by the present inventors. Samples prepared in this example showed high conductivity related to very sharp absorbance peaks under characterization of THz-TDS. The copper SRR sample exhibited magnetic resonance leading to negative permeability at 0.43 THz and plasmonic resonances leading to negative permittivity at 0.98 THz while copper break-microstrips exhibited plasmonic resonances at 0.68 THz.

Example 2

Three-dimensional alternative-stacking nanogold Left-handed metamaterials with structure lattice size of 200 micron were designed and evaluated using a THz spectroscopy system. The fabrication steps for the metamaterials are elaborated as follows.

Figure 11:
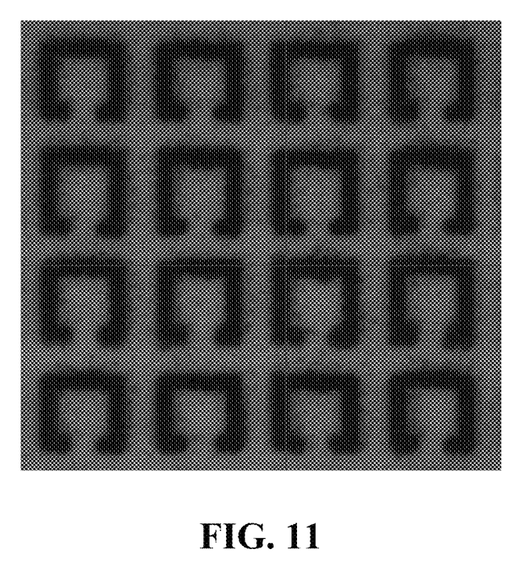
FIG. 11 is a photograph of a SRR (p=180 µm) deposited on Kodak EasyShare matte photopaper wherein the deposited material is dodecanethiol functionalized nano-gold in accordance with an aspect of the present disclosure.

Now referring to FIG. 11, a SRR (p=180 μm) was deposited on Kodak EasyShare matte photopaper. The deposited material was dodecanethiol functionalized nanogold having 4-5 nm particle size in 2% in toluene having ~10 cps viscosity. The drop size was ~30 μm using a 1 pL cartridge. Thickness of the structures was 38.7 nm. The image was taken by a built in Fiducial camera.

Figure 12:
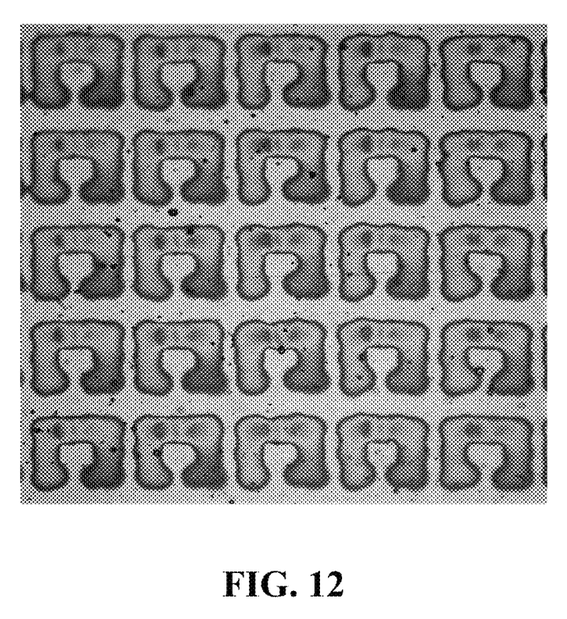
FIG. 12 is a photograph of a SRR (p=80 µm) deposited on 127 µm thick polyimide substrate wherein the deposited material is conductive polymer PEDT/PSS with ~11 cps viscosity in accordance with an aspect of the present disclosure.

Now referring to FIG. 12, a SRR (p=80 μm) was deposited on a 127 μm thick polyimide substrate. The deposited material was a conductive polymer PEDT/PSS with ~11 cps viscosity. The drop size was ~18 μm using a 1 pL cartridge. The thickness of the structure was 0.7 μm. The image magnification is 20× using a bright field microscope.

Figure 13:
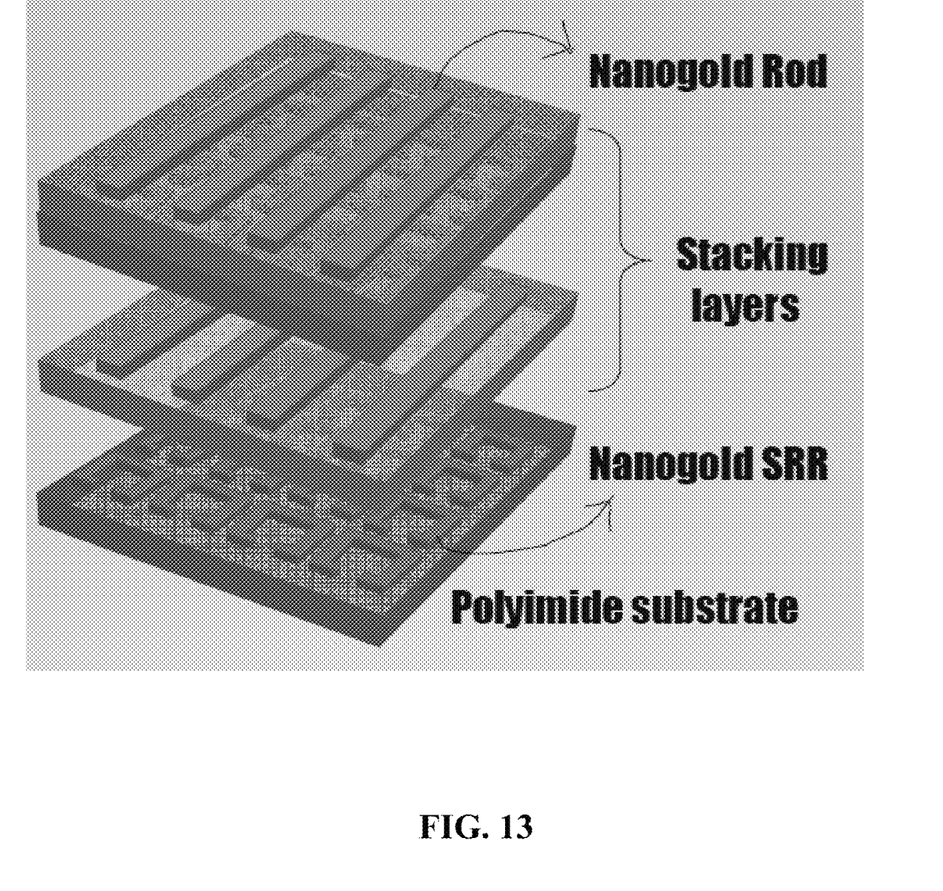
FIG. 13 is a graphical depiction of a three-dimensional multilayer LHM having a structural size of p=200 µm deposited on 54 µm thick polyimide substrate and ~43 µm thick adhesive clear polymer as the stacking layers in accordance with an aspect of the present disclosure.

Now referring to FIG. 13, depicted is a three-dimensional multilayer LHM with a structural size of p=200 μm deposited on a 54 μm thick polyimide substrate and ~43 μm thick adhesive clear polymer as the stacking layers. The deposited material was dodecanethiol functionalized nanogold having a 4-5 nm particle size, in 2% toluene, having ~10 cps viscosity. The drop size was ~30 μm using a 1 pL cartridge. The thickness of each structure was 38.7 μm. Number of stack layers: five plus the base.

Figure 14:
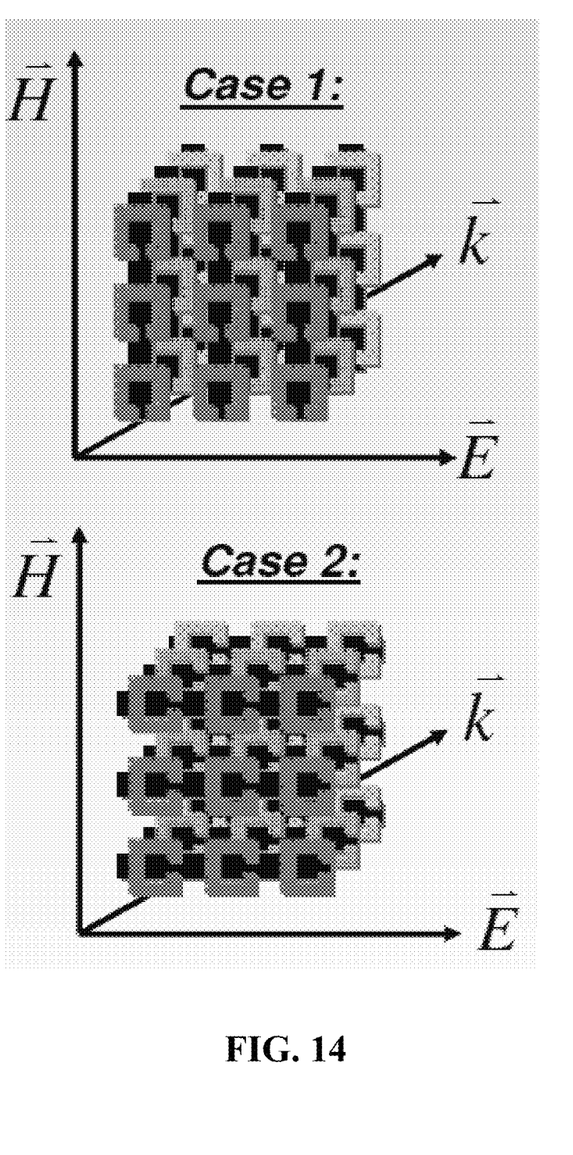
FIG. 14 is a graphical depiction of a case 1 orientation (top) of a sample relative to incident THz wave propagation wherein the E-field is perpendicular to rod and case 2 (bottom) wherein the E-field is parallel to the rod in accordance with an aspect of the present disclosure.
Figure 15:
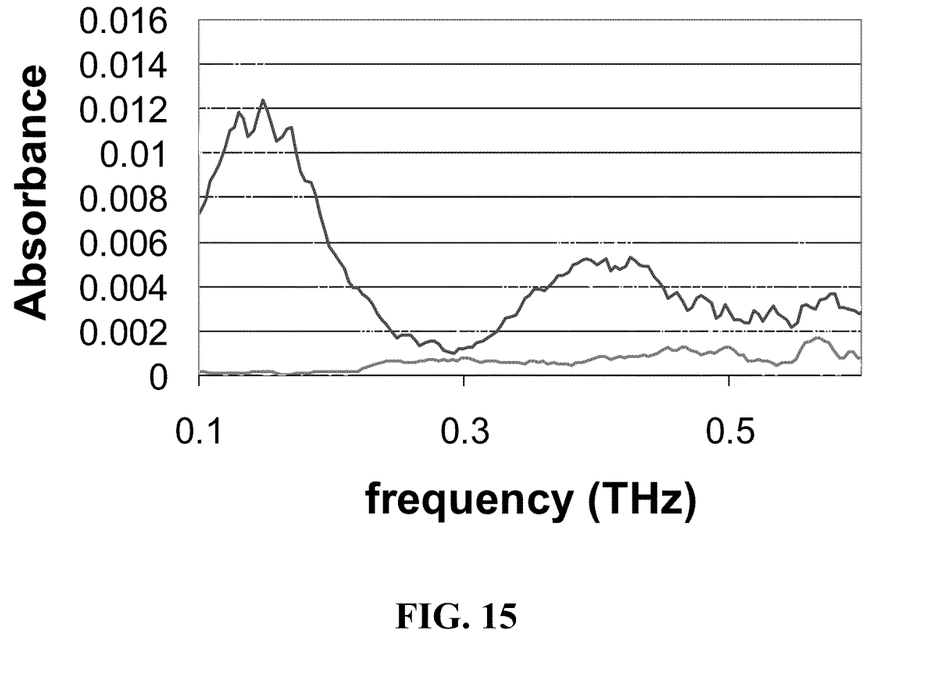
FIG. 15 is a graphical depiction of frequency resonance at 0.15 and 0.4 THz for symmetry oriented with E-field in accordance with an aspect of the present disclosure.

A T-Ray 2000 Spectroscopy system as described was used to evaluate the sample in transmission mode. A mode-locked Ti: Sapphire laser provided 80 fs pulses with wavelength of 780 nm at a repetition rate of about 80 MHz directed into a grating dispersion compensator (GDC) which added negative dispersion to the pulses. Now referring to FIG. 14, a THz pulse was generated by illuminating a biased photoconductive switch with the optical pulses and detected by a second photoconductive switch. The sample was scanned in case 1 (top) (E-field is perpendicular to rod) and case 2 (bottom (E-field is parallel to the rod). The time-domain waveform was recorded and then Fourier transformed to yield a frequency power spectrum. As shown in FIG. 15, this microfluidic-jetted fabricated metamaterial possesses a frequency resonance center at 0.15 and 0.4 THz for symmetry oriented with the E-field.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

All references cited herein are incorporated by reference herein.

What is claimed is:

1. A flexible left-handed metamaterial (LHM) having a negative index of refraction comprising at least two flexible substrates, wherein each flexible substrate comprises at least one material deposited thereon wherein the deposited material is selected for properties operable to act as a metamaterial having a negative effective permittivity and permeability and the deposited material is deposited in a pattern operable to act as a metamaterial having a negative effective permittivity and permeability when the at least two flexible substrates are layered one on top of the other, wherein the LHM comprises a negative effective permittivity at 0.68 to 0.98 THz and a negative effective permeability at 0.43 THz.

2. The flexible left-handed metamaterial of claim 1 wherein the at least two flexible substrates are selected from a polyimide, polyester, and copper-clad polyimide.

3. The flexible left-handed metamaterial of claim 1 wherein the deposited material comprises at least one of a metal, a Group III-V semiconductor, a highly electrically conductive polymer, a highly electrically conductive liquid metal, a nanometallic particle, a metallic single-walled carbon nanotube, a semiconductor single walled carbon nanotube, a metallic multi-walled carbon nanotube, a semiconductor multi-walled carbon nanotube, colloidal graphite, and colloidal silver liquid.

4. The flexible left-handed metamaterial of claim 1 wherein the deposited material is selected from at least one of gold, copper, silver, selenium, tellurium, germanium, silicon, beryllium, cadmium, zinc, arsenic, phosphorus, boron, aluminium, poly(3,4-ethylenedioxythiophene)poly(styrenesulfonate) (PEDOT:PSS), (3,4-ethylenedioxythiophene)-block-poly(ethylene glycol), indium tin oxide, gallium, nano-silver, nano-gold, metallic or semiconductor single walled carbon nanotubes, metallic or semiconductor multi-walled carbon nanotubes, colloidal graphite and colloidal silver liquid.

5. The flexible left-handed metamaterial of claim 1 wherein the deposited material comprises a functionalized nanoparticle.

6. The flexible left-handed metamaterial of claim 3 wherein the deposited material comprises a carrier.

7. The flexible left-handed metamaterial of claim 6 wherein the carrier comprises a fluid selected from dodecanethiol, toluene, xylene, 4-methylpentan-2-one, ethanol, hexane, butyl acetate, acetone, hexone, 2-propanol, deionized water, 4-methyl-2-pentanone, isobutyl methyl ketone, propylene glycol, monoethyl ether, ethyl acetate, propylene carbonate, and nitromethane.

8. The flexible left-handed metamaterial of claim 1 wherein the deposited material is deposited in a pattern selected from a periodic split-ring resonator (SRR), periodic microstrip, periodic monolithic rod, periodic horseshoe, periodic polygonal, periodic windmill, periodic swastika, periodic circular, periodic oval, and periodic square grid.

9. The flexible left-handed metamaterial of claim 1 wherein the pattern formed on the flexible substrates is alternating as between the layered substrates such that a first flexible substrate comprises a SRR or a periodic microstrip pattern and an adjacent flexible substrate comprises a SRR or periodic microstrip pattern that is other than the first layer.

10. A three-dimensional left-handed metamaterial (LHM) having a negative index of refraction comprising at least two substrates layered one on top of the other, wherein each substrate comprises at least one material deposited thereon selected for properties operable to act as a metamaterial having a negative effective permittivity and permeability and the deposited material of a first of the at least two substrates is deposited in either a SRR pattern or a periodic microstrip pattern and the deposited material of an adjacent second of the at least two substrates is deposited in either a SRR pattern or a periodic microstrip pattern that is other than the pattern deposited on the first substrate, wherein the LHM comprises a negative effective permittivity at 0.68 to 0.98 THz and a negative effective permeability at 0.43 THz.

11. The three-dimensional left-handed metamaterial of claim 10 wherein the substrate is selected from a polyimide, polyester, and copper clad polyimide.

12. The three-dimensional left-handed metamaterial of claim 10 wherein the deposited material comprises at least one of a metal, a Group III-V semiconductor, a highly electrically conductive polymer, a highly electrically conductive liquid metal, a nanometallic particle, a metallic single-walled carbon nanotube, a semiconductor single walled carbon nanotube, a metallic multi-walled carbon nanotube, a semiconductor multi-walled carbon nanotube; colloidal graphite, and colloidal silver liquid.

13. The three-dimensional left-handed metamaterial of claim 10 wherein the deposited material is selected from at least one of gold, copper, silver, selenium, tellurium, germanium, silicon, beryllium, cadmium, zinc, arsenic, phosphorus, boron, aluminum, poly(3,4-ethylenedioxythiophene)poly(styrenesulfonate) (PEDOT:PSS), (3,4-ethylenedioxythiophene)-block-poly(ethylene glycol), indium tin oxide, gallium, nano-silver, nano-gold, metallic or semiconductor single walled carbon nanotubes, metallic or semiconductor multi-walled carbon nanotubes, colloidal graphite and colloidal silver liquid.

14. The three-dimensional left-handed metamaterial of claim 10 wherein the deposited material comprises dodecanethiol-functionalized nanogold.

15. The three-dimensional left-handed metamaterial of claim 12 wherein the deposited material comprises a carrier.

16. The three-dimensional left-handed metamaterial of claim 15 wherein the carrier comprises a fluid selected from dodecanethiol, toluene, xylene, 4-methylpentan-2-one, ethanol, hexane, butyl acetate, acetone, hexone, 2-propanol, deionized water, 4-methyl-2-pentanone, isobutyl methyl ketone, propylene glycol, monoethyl ether, ethyl acetate, propylene carbonate, and nitromethane.

* * * * *